United States Patent
Xu

(10) Patent No.: US 10,221,444 B1
(45) Date of Patent: Mar. 5, 2019

(54) METHODS AND SYSTEMS FOR PRODUCTION OF DNA LIBRARIES DIRECTLY FROM FFPE TISSUE

(71) Applicant: URIT Medical Electronic Co., Ltd., Guilin, Guangxi (CN)

(72) Inventor: Tom Cheng Xu, Castro Valley, CA (US)

(73) Assignee: URIT Medical Electronic Co., Ltd., Guilin (CN)

( * ) Notice: Subject to any disclaimer, the term of this patent is extended or adjusted under 35 U.S.C. 154(b) by 0 days.

(21) Appl. No.: 16/053,655

(22) Filed: Aug. 2, 2018

Related U.S. Application Data

(60) Provisional application No. 62/581,713, filed on Nov. 5, 2017.

(51) Int. Cl.
*C12Q 1/6806* (2018.01)
*C12N 15/10* (2006.01)

(52) U.S. Cl.
CPC ....... *C12Q 1/6806* (2013.01); *C12N 15/1003* (2013.01)

(58) Field of Classification Search
None
See application file for complete search history.

(56) References Cited

U.S. PATENT DOCUMENTS

2018/0127811 A1* 5/2018 Benson .................. C09B 15/00

OTHER PUBLICATIONS

Promega (PCR Amplification Protocols and background information about PCR and RT-PCR downloaded from the internet Nov. 20, 2018; public availability date Oct. 2, 2004) (Year: 2004)*
Killelea et al (frontiers in microbiology 5:1-11) (Year: 2014).*
Kandyala, R., et al., "Xylene: An overview of its health hazards and preventive measures," Journal of Oral and Maxillofacial Pathology, 14(1):1, 2010.

* cited by examiner

*Primary Examiner* — Christopher M Gross
(74) *Attorney, Agent, or Firm* — Levine Bagade Han LLP

(57) ABSTRACT

Disclosed are methods and compositions for preparing a DNA library from slide-mounted FFPE tissue samples for downstream next-generation sequencing. In one embodiment, a method of preparing the DNA library is disclosed. The method can comprise applying a droplet of a reagent mixture onto a slide-mounted FFPE tissue sample. The reagent mixture can comprise one or more buffer solutions, a cofactor, a nonionic surfactant, a glycerol solution, a gelatin solution, dNTPs, a DNA polymerase, and a primer pool comprising a plurality of forward primers and reverse primers. The method can also comprise stirring the droplet in a circular motion on the slide while scraping portions of the FFPE tissue sample mounted on the slide to yield a reaction mixture. The method can further comprise aspirating the reaction mixture from the slide directly into a pipette tip and dispensing the reaction mixture into a reaction vessel for further amplification.

14 Claims, 12 Drawing Sheets

METHODS AND SYSTEMS FOR PRODUCTION OF DNA LIBRARIES DIRECTLY FROM FFPE TISSUE

CROSS-REFERENCE TO RELATED APPLICATION

This application claims the benefit of priority to U.S. Provisional Patent Application No. 62/581,713, filed on Nov. 5, 2017, the content of which is hereby incorporated by reference in its entirety.

TECHNICAL FIELD

The present disclosure relates generally to the field of tissue sample preparation for genetic sequencing; more specifically, to methods and compositions for producing deoxyribonucleic acid (DNA) libraries directly from formalin-fixed paraffin-embedded (FFPE) tissue samples.

BACKGROUND

FFPE tissue is one of the most important sources of DNA and ribonucleic acid (RNA) for clinical cancer diagnosis and research. Such diagnosis and research is often done using advanced genetic sequencing techniques known as next-generation sequencing (NGS). Diagnostic procedures involving NGS often involve detecting low frequency somatic mutations in a DNA library prepared from one or more FFPE tissue samples, such mutations being key indicators of cancer progression in patients.

One of the more popular methods of preparing such a DNA library involves purifying genomic DNA using the QIAamp® DNA FFPE Tissue Kit distributed by QIAGEN Gmbh. Another popular method involves use of the Ion AmpliSeq® Direct FFPE DNA Kit distributed by Thermo Fisher Scientific Inc. However, all such tissue preparation kits and their accompanying procedures are fraught with challenges.

For example, FIG. 1 shows certain steps of a known method of preparing DNA libraries from FFPE tissue samples. The steps shown in FIG. 1 are similar to certain steps of a library preparation procedure involving the QIAamp® DNA FFPE Tissue Kit. Such procedures often require tissue from multiple slide-mounted FFPE samples. This can quickly exhaust a specimen supply when multiple NGS runs are required. The FFPE slides are also deparaffinized in an aromatic solvent such as xylene. However, the health hazards of xylene are well documented and those with long-term exposure to xylene can develop headaches, dizziness, nausea, and vomiting (see Kandyala, R., Raghavendra, S. P. C., & Rajasekharan, S. T. (2010). Xylene: An overview of its health hazards and preventive measures. *Journal of Oral and Maxillofacial Pathology*, 14(1):1). Once deparaffinized, the FFPE slides are washed in ethanol to displace the xylene-based solution and the exposed tissue samples on the slides are then scraped off with a scalpel or razor blade and transferred to a test tube or reaction tube. The collected tissue sample is then subjected to a proteinase K digestion step to digest contaminating proteins and a lysis buffer is added to lyse remaining contaminating cellular components. The lysate is then transferred to a reaction tube comprising a mini-column made of silica membrane. Additional buffers are then added to the reaction tube and the entire tube is centrifuged to bind the DNA from the tissue sample to the mini-column. The mini-column is then transferred to a collection tube and an elution buffer is added. The tube is finally centrifuged to elute the DNA from the mini-column. DNA amplification reagents can then be added to the eluted DNA and such a mixture can then be subjected to an amplification reaction to yield the DNA library.

As can be seen from FIG. 1, current methods of preparing DNA libraries from FFPE tissue samples are often laborious and time-consuming (e.g., up to 72 hours). Such methods also require multiple reagents and buffers and are susceptible to high risks of clinician error. While other methods, such as those involving the Ion AmpliSeq® Direct FFPE DNA Kit, have eliminated the deparaffinization step with xylene, such methods require the FFPE tissue sample to be dissolved in mineral oil and require multiple reagents and a heating step to extract DNA from the tissue sample. Additional steps are then required to prepare the extracted DNA for further amplification using reagents from a separate DNA amplification kit.

Therefore, a solution is needed which reduces the number of operational steps needed to prepare DNA libraries from slide-mounted FFPE tissue samples yet maintain or improve the quantity and quality of target sequence yields compared to convention methods. Such a solution should be cost-effective compared to conventional methods, require less time, and should lessen the risk of clinician or operator error.

SUMMARY

Disclosed herein are methods and compositions for the production of DNA libraries directly from substrate-mounted (e.g., slide-mounted) FFPE tissue samples. In one embodiment, a method of preparing a DNA library is disclosed comprising applying a droplet of a reagent mixture onto a substrate-mounted formalin-fixed paraffin-embedded (FFPE) tissue sample. For example, the FFPE tissue sample can be mounted on a slide such as a glass slide.

In one embodiment, the droplet of the reagent mixture applied onto the FFPE tissue sample can be applied using a wide orifice pipette tip coupled to a pipette. The wide orifice pipette tip can have an orifice inner diameter of between about 1.00 mm to about 1.25 mm.

The droplet of the reagent mixture can be applied on to the FFPE tissue sample when the FFPE tissue sample is at a temperature of between about 0° C. and about 23° C. In one embodiment, the droplet of the reagent mixture applied onto the FFPE tissue sample can be about 20 microliters (µL) in volume.

In some embodiments, the reagent mixture can comprise one or more buffer solutions, a cofactor, a nonionic surfactant, a glycerol solution, a gelatin solution, a plurality of dNTPs, a DNA polymerase, and a primer pool comprising a plurality of forward primers and reverse primers.

The method can also comprise stirring the droplet of the reagent mixture in a circular motion on the slide while scraping portions of the FFPE tissue sample mounted on the slide to yield a reaction mixture comprising the reagent mixture and portions of the FFPE tissue sample. In some embodiments, the droplet of the reagent mixture can be stirred on the slide in a clockwise circulation motion, a counterclockwise circular motion, or a combination thereof. The same wide orifice pipette tip can also be used to stir the droplet of the reagent mixture on the slide while also scraping the portion of the FFPE tissue sample mounted on the slide. The droplet of the reagent mixture on the slide can be stirred for between about 1 minute to 5 minutes prior to aspirating the reaction mixture.

The method can further comprise aspirating the reaction mixture from the slide directly into a pipette tip and dispensing the reaction mixture into a reaction vessel. In some embodiments, the reaction mixture can be aspirated into the wide orifice pipette tip and dispensed into the reaction vessel from the wide orifice pipette tip.

The method can also comprise subjecting the reaction mixture in the reaction vessel to a polymerase chain reaction (PCR) protocol. The PCR protocol can comprise the steps of: (i) heating the reaction mixture at a first temperature to activate the DNA polymerase in an activation step; (ii) further heating the reaction mixture at a second temperature to denature nucleic acids within the reaction mixture in a denaturation step; (iii) lowering the temperature to a third temperature to allow for annealing and extension; and (iv) repeating steps (ii) and (iii) for at least 24 cycles.

In one or more embodiments, the first temperature of the PCR protocol can be about 95° C., the second temperature of the PCR protocol can be about 99° C., and the third temperature of the PCR protocol can be about 60° C.

In one or more embodiments, the method disclosed herein can be applied to FFPE tissue samples comprising at least one of a FFPE bladder tissue sample, a FFPE breast tissue sample, a FFPE cervical tissue sample, a FFPE colorectal tissue sample, a FFPE esophageal tissues sample, a FFPE gastric tissue sample, a FFPE renal tissue sample, a FFPE hepatic tissue sample, a FFPE lung squamous tissue sample, a FFPE lymphoid tissue sample, a FFPE skin tissue sample, a FFPE nasopharyngeal tissue sample, a FFPE ovarian tissue sample, a FFPE prostate tissue sample, and a FFPE thyroid tissue sample.

In another embodiment, a method of preparing a PCR mixture comprising a FFPE tissue sample is also disclosed. The method comprises applying a droplet of a reagent mixture onto the FFPE tissue sample. The FFPE tissue sample can be mounted on a substrate such as a slide. In one embodiment, the droplet of the reagent mixture onto the FFPE tissue sample can be applied using a wide orifice pipette tip coupled to a pipette. The wide orifice pipette tip can have an orifice inner diameter of between about 1.00 mm to about 1.25 mm.

The droplet of the reagent mixture can be applied on to the FFPE tissue sample when the FFPE tissue sample is at a temperature of between about 0° C. and about 23° C. In one embodiment, the droplet of the reagent mixture applied onto the FFPE tissue sample can be about 20 microliters (μL) in volume.

In some embodiments, the reagent mixture can comprise one or more buffer solutions, a cofactor, a nonionic surfactant, a glycerol solution, a gelatin solution, a plurality of dNTPs, a DNA polymerase, and a primer pool comprising a plurality of forward primers and reverse primers.

The method can also comprise stirring the droplet of the reagent mixture in a circular motion on the slide while scraping portions of the FFPE tissue sample mounted on the slide to yield a PCR mixture comprising the reagent mixture and portions of the FFPE tissue sample. In some embodiments, the droplet of the reagent mixture can be stirred on the slide in a clockwise circulation motion, a counterclockwise circular motion, or a combination thereof. The same wide orifice pipette tip can also be used to stir the droplet of the reagent mixture on the slide while also scraping the portion of the FFPE tissue sample mounted on the slide. The droplet of the reagent mixture on the slide can be stirred for between about 1 minute to 5 minutes prior to aspirating the PCR mixture.

The method can further comprise aspirating the PCR mixture from the slide directly into a pipette tip and dispensing the PCR mixture into a reaction vessel. In some embodiments, the PCR mixture can be aspirated into the wide orifice pipette tip and dispensed into the reaction vessel from the wide orifice pipette tip.

In another embodiment, a reagent solution for use in processing a slide-mounted FFPE tissue sample is disclosed. The reagent solution can comprise a tris(hydroxymethyl) aminomethane (Tris)-hydrochloric acid (HCl) buffer solution, a potassium chloride (KCl) buffer solution, a magnesium chloride ($MgCl_2$) solution, a polysorbate 20 solution, a glycerol solution, a 2gelatin solution, a plurality of dNTPs, and a Taq DNA polymerase.

In one embodiment, the Tris-HCl buffer solution can be a Tris-HCl buffer solution at a pH of about 8.0 and a concentration of between about 60.0 mM and about 90.0 mM. In this and other embodiments, the KCl buffer solution can have a concentration of between about 100.0 mM and about 150.0 mM.

In some embodiments, the $MgCl_2$ solution can have a concentration of between about 2.0 mM and about 5.0 mM. In one or more embodiments, the polysorbate 20 solution can be between about 0.01% (v/v) to about 0.30% (v/v) of the total volume of the reagent solution. In these and other embodiments, the glycerol solution can be between about 10.0% (v/v) and about 30.0% (v/v) of the total volume of the reagent solution. In some embodiments, the gelatin solution can be between about 0.01% (v/v) and about 0.80% (v/v) of the total volume of the reagent solution.

DETAILED DESCRIPTION

Disclosed herein are methods and compositions for the efficient preparation of DNA libraries directly from slide-mounted FFPE tissue samples. A DNA library is a collection of genomic DNA sequences of interest obtained from a tissue sample of an organism. The methods and compositions disclosed herein are optimized for the preparation of DNA libraries for further downstream next-generation sequencing (NGS) for cancer diagnosis and research. The DNA libraries generated from the methods and compositions disclosed herein can be used with any number of NGS platforms, including platforms requiring immobilization of DNA fragments onto a solid support, cyclic sequencing reactions using automated devices, and detection of sequences using imaging or semiconductor technologies. For example, the DNA libraries generated from the methods and compositions disclosed herein can be used with an Illumina® sequencing by synthesis (SBS) NGS platform (e.g., an Illumina MiniSeq®, MiSeq®, or NextSeq® system) distributed by Illumina, Inc., an Ion Personal Genome Machine® (PGM) system distributed by Thermo Fisher Scientific Inc., a SOLiD® NGS system distributed by Thermo Fisher Scientific Inc., or a combination thereof.

Figure 1:
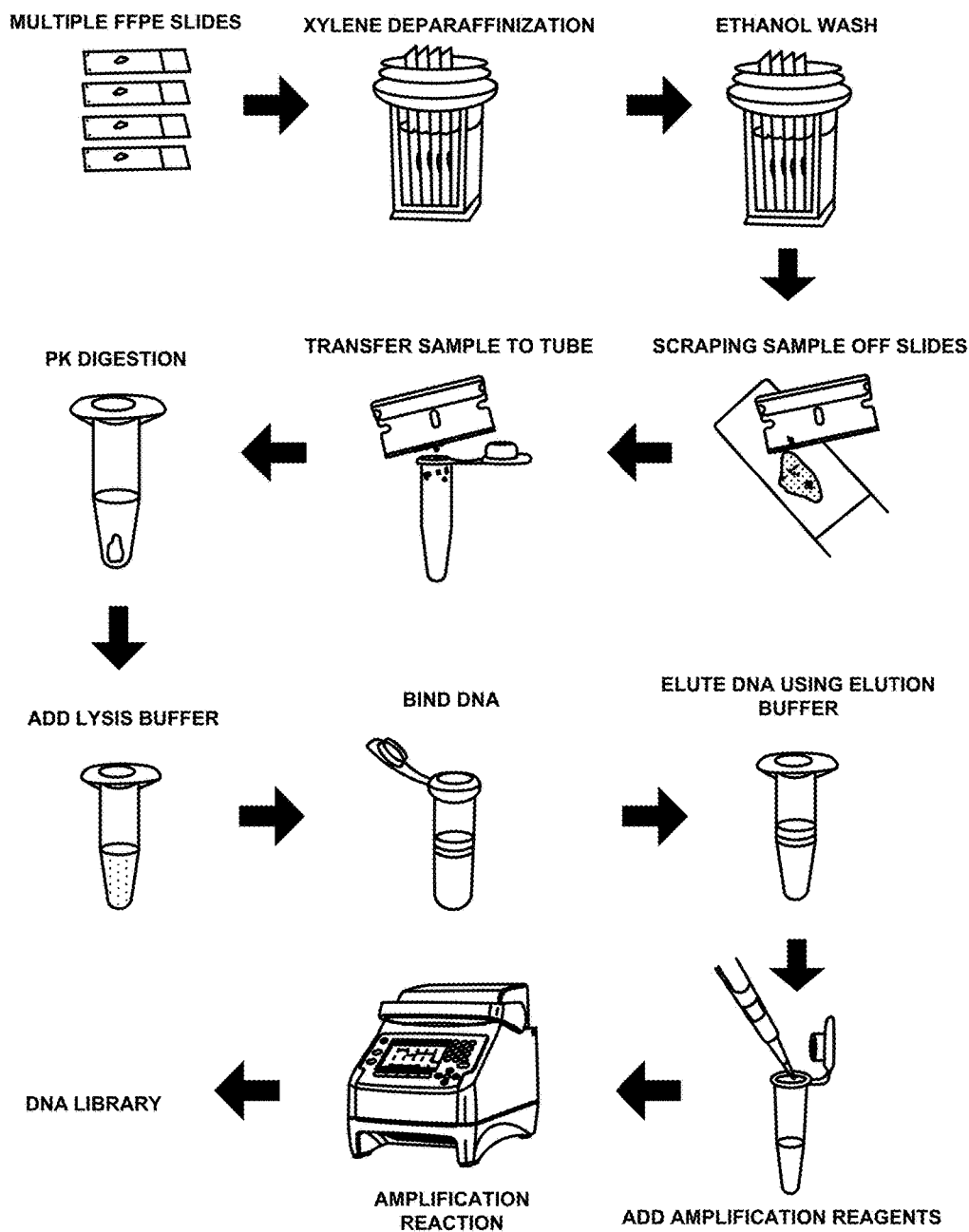
FIG. 1 illustrates a method known in the art for preparing a DNA library from slide-mounted FFPE tissue samples.
Figure 2:
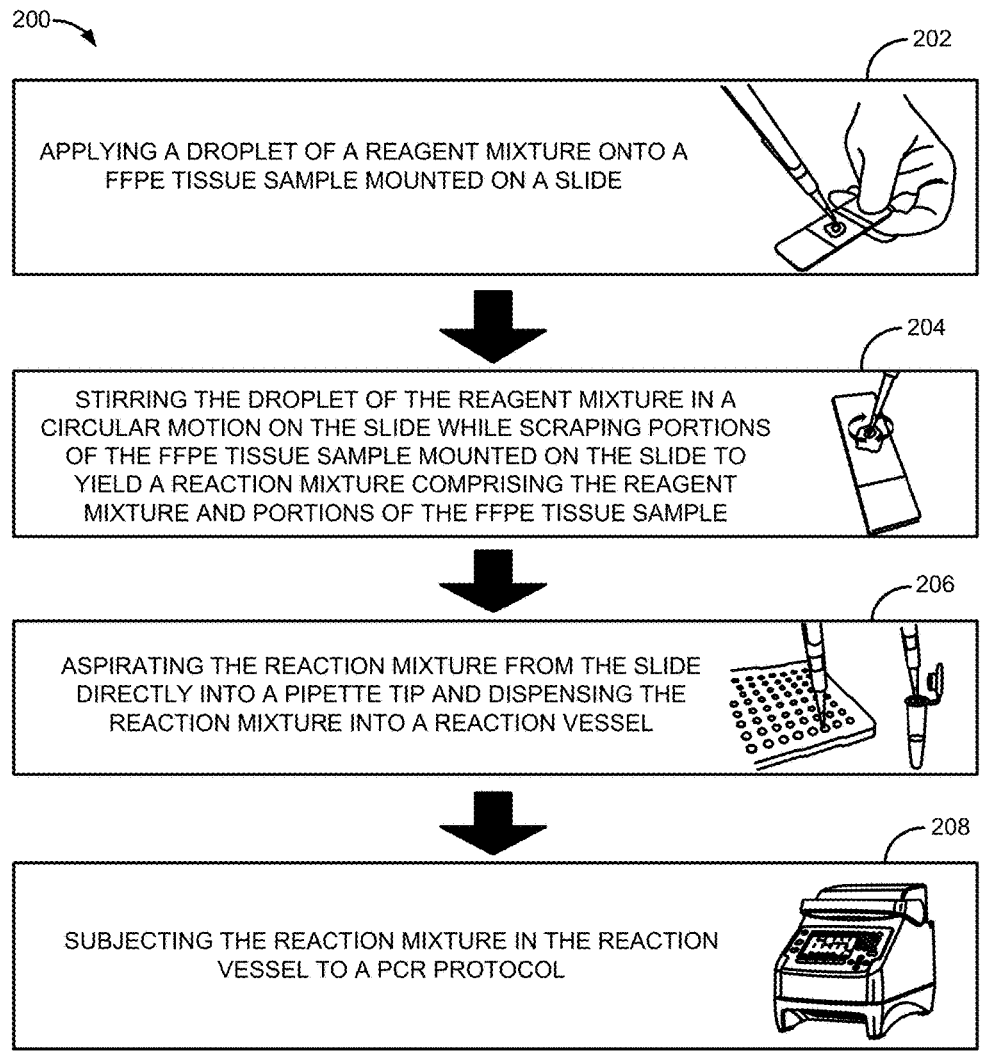
FIG. 2 illustrates an embodiment of an improved method of preparing a DNA library from a slide-mounted FFPE tissue sample.
Figure 3A:
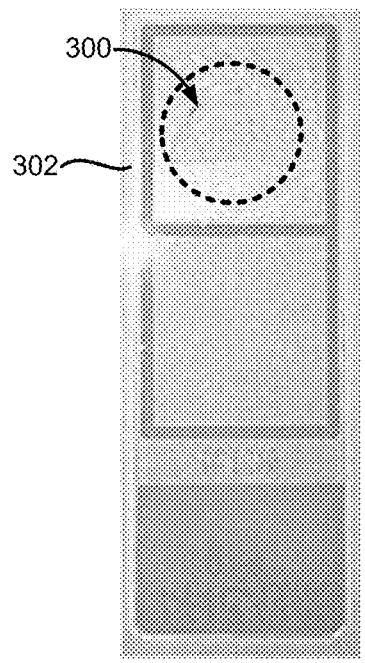
FIG. 3A is a black-and-white image of a slide-mounted FFPE tissue sample.

FIG. 2 illustrates an embodiment of an improved method 200 of preparing a DNA library from a FFPE tissue sample 300 (see FIG. 3A) mounted on a solid substrate 302 (see FIG. 3A). The method 200 can comprise applying a droplet 412 of a reagent mixture 402 (see FIGS. 4A, 4B, and 5) onto a formalin-fixed paraffin-embedded (FFPE) tissue sample 300 (see FIG. 3A) mounted on the solid substrate 302 in step 202. In some embodiments, the solid substrate 302 can be a glass slide (e.g., a glass microscope slide), an inert polymeric slide, or a combination thereof.

Figure 4A:
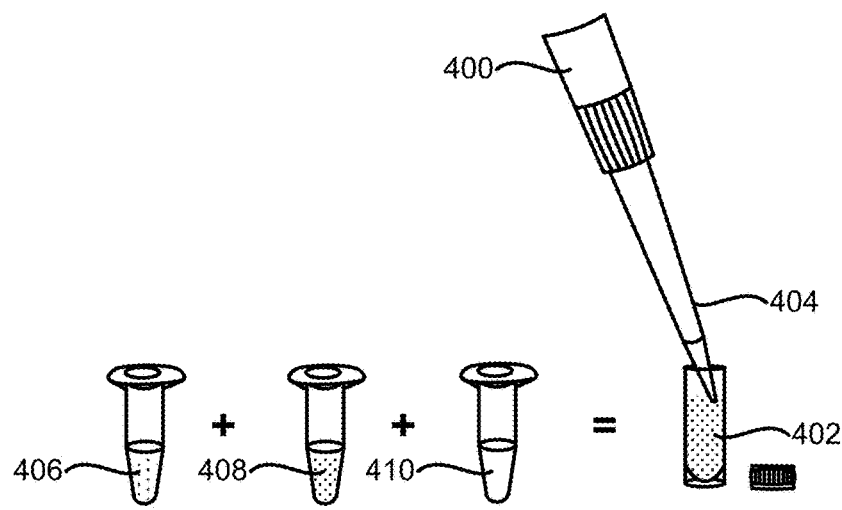
FIG. 4A illustrates a pipette aspirating a reagent mixture into a pipette tip.
Figure 4B:
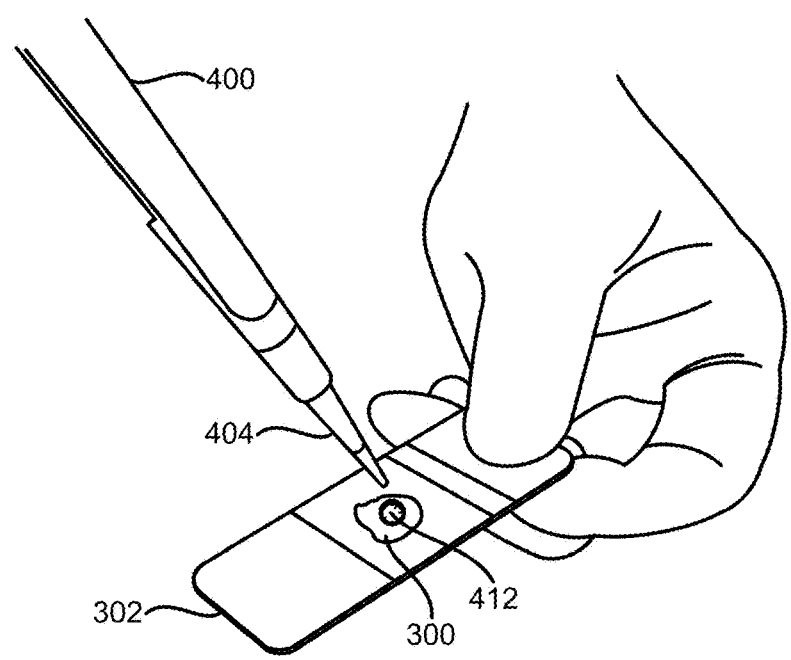
FIG. 4B illustrates a pipette applying a droplet of the reagent mixture onto a slide-mounted FFPE tissue sample.

The droplet 412 of the reagent mixture 402 can be applied using a pipette 400 having a pipette tip 404 (see FIGS. 4A and 4B). In some embodiments, the pipette tip 404 used to apply the droplet 412 can be a wide orifice pipette tip 900 (see FIG. 9) coupled to the pipette 400. In these and other embodiments, the wide orifice pipette tip 900 can have an orifice inner diameter 904 (see FIG. 9) of between about 1.00 mm to about 1.25 mm.

The droplet 412 of the reagent mixture 402 can be applied on to the slide-mounted FFPE tissue sample 300 when the slide-mounted FFPE tissue sample 300 is retrieved from a cold storage receptacle such as a refrigerator, a refrigerated storage, a cooler or cooling container, or a combination thereof. In these embodiments, the slide-mounted FFPE tissue sample 300 can be at a temperature of between about 0° C. and about 20° C. Alternatively, the droplet 412 of the reagent mixture 402 can be applied on to the slide-mounted FFPE tissue sample 300 when the FFPE tissue sample 300 is at room temperature (or between about 20° C. and about 25° C.). Applying the droplet 412 of the reagent mixture 402 onto the slide-mounted FFPE tissue sample 300 will be discussed in more detail in the following sections.

In some embodiments, the reagent mixture 402 can comprise a reagent solution 406 (see FIG. 4A) and a primer pool solution 408 (see FIG. 4A) comprising a plurality of forward primers and reverse primers for the target sequences of interest. The reagent solution 406 can comprise one or more buffer solutions, a cofactor, a nonionic surfactant, a glycerol solution, a gelatin solution, a plurality of dNTPs, and a DNA polymerase. In certain embodiments, the one or more buffer solutions can comprise a tris(hydroxymethyl)aminomethane (Tris) buffer solution (e.g., a Tris-hydrochloric acid (HCl) buffer solution), a potassium chloride (KCl) buffer solution, or a combination thereof.

In some embodiments, the cofactor or cofactor solution can be magnesium chloride ($MgCl_2$) solution. The nonionic surfactant can be a polysorbate solution (e.g., a polysorbate 20 solution). More specifically, the nonionic surfactant can be a Tween® 20 surfactant distributed by Sigma-Aldrich, Inc., a Montanox™ 20 surfactant distributed by SEPPIC S.A., or an Alkest® 20 surfactant distributed by Oxiteno S.A.

In some embodiments, the DNA polymerase can be a thermostable DNA polymerase such as a Taq DNA polymerase. More specifically, the Taq DNA polymerase is a hot start Taq DNA polymerase configured for a hot start PCR protocol. For example, the Taq DNA polymerase can be a TrueStart™ hot start Taq DNA polymerase distributed by Thermo Fisher Scientific Inc. or a JumpStart™ hot start Taq DNA polymerase distributed by Sigma-Aldrich, Inc.

As contemplated by this disclosure and as will be appreciated by one of ordinary skill in the art, the reagent solution 406 can be made at different concentrations and provided as 1× to 5× (e.g., 1×, 2×, 3×, 4×, or 5×) master mixes. Presented in Table 1 below is an example formulation of a reagent solution 406:

TABLE 1

| Example Composition of 2× Reagent Solution | |
|---|---|
| Solution Component | Concentration |
| Tris-HCl, pH 8.0 | 60.0 mM-90.0 mM |
| KCl | 100.0 mM-150.0 mM |
| $MgCl_2$ | 2.0 mM-5.0 mM |
| Polysorbate 20 | 0.01%-0.30% (v/v) |
| Glycerol | 10.0%-30.0% (v/v) |
| Gelatin | 0.01%-0.80% (v/v) |
| dNTPs (dATP, dCTP, dGTP, and dTTP) | 1.0 mM-3.0 mM |
| Hot start Taq DNA polymerase | 0.5 Units/µL-0.8 Units/µL |

One unexpected discovery made by the applicant is that the reagent solution having the composition disclosed herein is effective in facilitating the release of biopsied tissue samples fixed by paraffin on a solid substrate without unduly interfering with the quality of the nucleic acids preserved within such tissue samples. Another unexpected discovery made by the applicant is that the reagent solution having the composition disclosed herein is ideal for application in droplet form (and later for stirring) on slide-mounted FFPE tissue samples without the reagent solution inadvertently running or flowing off the slide.

In some embodiments, the reagent mixture 402 can be comprised of a 50% (v/v) 2× reagent solution 406, a 20% (v/v) 5× primer pool solution 408, and 30% (v/v) deionized water 410. In these and other embodiments, the droplet 412 of the reagent mixture 402 can have a droplet volume of about 20 microliters (µL). Presented in Table 2 below is an example formulation of a 20 µL droplet 412 of the reagent mixture 402 applied to the FFPE tissue sample 300:

TABLE 2

Example Droplet Composition

| Droplet Component | Volume | Percentage of Total Volume |
|---|---|---|
| 2× Reagent Solution | 10 µL | 50% |
| 5× Primer Pool | 4 µL | 20% |
| Deionized water | 6 µL | 30% |
| TOTAL: | 20 µL | 100% |

In some embodiments, the primer pool solution 408 can comprise forward primers and reverse primers. For example, the primer pool solution 408 can comprise between 100 and 200 primer pairs (forward primers and reverse primers) targeting certain genetic sequences of interest. In other embodiments, the primer pool solution 408 can comprise between 200 and 300 primer pairs.

The method 200 can further comprise stirring the droplet 412 of the reagent mixture 402 in a circular motion 600 (see FIG. 6A) on the solid substrate 302 while scraping portions of the FFPE tissue sample 300 mounted on the solid substrate 302 to yield a reaction mixture 602 comprising the reagent mixture 402 and portions of the FFPE tissue sample 300 in step 204.

In some embodiments, the droplet 412 of the reagent mixture 402 can be stirred on the solid substrate 302 in a clockwise circulation motion, a counterclockwise circular motion, or a combination thereof. The same pipette tip 404 used to apply the droplet 412 (see FIG. 4B) can be used to stir the droplet 412 of the reagent mixture 402 on the solid substrate 302 while simultaneously scraping portions of the slide-mounted FFPE tissue sample 300. In certain embodiments, the same wide orifice pipette tip 900 used to apply the droplet 412 can also be used to stir the droplet 412 of the reagent mixture 402 on the solid substrate 302 while simultaneously scraping portions of the slide-mounted FFPE tissue sample 300 into the stirred droplet 412. The droplet 412 can be stirred and the FFPE tissue sample 300 can be scraped for between about 1 minute to about 5 minutes prior to aspirating the reaction mixture 602. More specifically, the droplet 412 can be stirred and the FFPE tissue sample 300 can be scraped for between about 2 minutes to about 3 minutes.

In one embodiment, the droplet 412 can be stirred in a substantially circular area or region of the solid substrate 302. In this embodiment, the droplet 412 can be stirred in a substantially circular area of approximately 20.0 mm$^2$ (i.e., the stirring is confined to a substantially circular region of the slide having an area of approximately 20.0 mm$^2$). In other embodiments, the droplet 412 can be stirred in a substantially circular area of between approximately 12.5 mm$^2$ and 40.0 mm$^2$. In some embodiments, the droplet 412 can also be stirred in a rectangular motion, an elliptic motion, a zig-zig motion, a spiraling motion, a figure-eight motion, or a combination thereof. After this stirring and scraping step, the reaction mixture 602 can be in the form of a slurry comprising the reagent mixture 402 and broken up pieces of the FFPE tissue sample 300.

One unexpected discovery made by the applicant is that one droplet 412 of the reagent mixture 402 can be applied directly on a slide-mounted FFPE tissue sample 300 and nucleic acids preserved within such a tissue sample can be extracted directly from the FFPE tissue sample 300 on the solid substrate 302 by simply stirring the droplet 412 according to the methods disclosed herein.

The method 200 can further comprise aspirating the reaction mixture 602 from the solid substrate 302 (e.g., the glass slide) directly into the pipette tip 404 and dispensing the reaction mixture 602 from the pipette tip 404 into a reaction vessel 800 (see FIGS. 8A and 8B) in step 206. In some embodiments, the reaction mixture 602 can be aspirated using a wide orifice pipette tip 900 (see FIG. 9) directly from the solid substrate 302 (e.g., the glass slide) into the wide orifice pipette tip 900. The reaction mixture 602 can then be dispensed from the wide orifice pipette tip 900 into the reaction vessel 800.

The reaction mixture 602 can be aspirated by drawing the pipette tip 404 over the stirred area in a substantially circular motion while slowly releasing a depressed plunger of the pipette 400. In other embodiments, the reaction mixture 602 can also be aspirated by drawing the pipette tip 404 over the stirred area in a substantially rectangular motion, an elliptic motion, a zig-zag motion, a spiraling motion, a figure-eight motion, or a combination thereof while slowly releasing a depressed plunger of the pipette 400.

In certain embodiments, the reaction vessel 800 can be a single PCR reaction tube or vessel. In other embodiments, the reaction vessel 800 can be one well of a multi-well PCR plate, such as a 96-well plate or a 384-well plate. The reaction mixture 602 within the reaction vessel 800 can be considered a PCR mixture or a PCR-ready mixture.

The method 200 can further comprise subjecting the reaction mixture 602 in the reaction vessel 800 to a polymerase chain reaction (PCR) protocol in step 208. The PCR protocol can comprise (i) heating the reaction mixture 602 at a first temperature to activate the DNA polymerase in an activation step. The PCR protocol can also comprise (ii) heating the reaction mixture 602 at a second temperature to denature template DNA within the reaction mixture 602 in a denaturation step. The PCR protocol can further comprise (iii) lowering the temperature to a third temperature to allow for annealing of the primers to the template DNA and extension or elongation of the annealed primers by the DNA polymerase. The PCR protocol can also comprise (iv) repeating the (ii) denaturation and (iii) annealing and extension steps for at least 24 cycles.

In some embodiments, the (ii) denaturation and (iii) annealing and extension steps can be repeated for 24 cycles. In other embodiments, the (ii) denaturation and (iii) annealing and extension steps can be repeated for between 25 cycles and 30 cycles.

In one or more embodiments, the PCR protocol can be a hot start PCR protocol and the DNA polymerase used in the reagent mixture 402 can be a hot start Taq DNA polymerase. In this and other embodiments, the first temperature of the hot start PCR protocol can be about 95° C. (i.e., the activation temperature can be about 95° C.), the second temperature of the hot start PCR protocol can be about 99° C. (i.e., the denaturation temperature can be about 99° C.), and the third temperature of the hot start PCR protocol can be about 60° C.

Presented in Table 3 below is an example hot start PCR protocol used to generate DNA libraries using the method 200 described herein:

TABLE 3

EXAMPLE HOT START PCR PROTOCOL

| Enzyme Activation Step | Denaturation Step | Annealing and Extension Steps | Cooling Step |
|---|---|---|---|
| Temp: ~95° C. Time: ~10 min. | Temp: ~99° C. Time: ~15 sec. | Temp: ~60° C. Time: ~4 min. Repeat: 24× | Temp: ~10° C. Time: TBD |

The amplified sequences obtained from the reaction vessel 800 after undergoing the aforementioned PCR protocol can then be used to generate DNA libraries for further downstream NGS reactions or protocols. For example, the amplified sequences obtained from the reaction vessel 800 after undergoing the aforementioned PCR protocol can be used to generate DNA libraries used as part of (but not limited to) an Illumina® NGS protocol, an Ion PGM® protocol, a SOLiD® NGS protocol, or a combination thereof.

One unexpected discovery made by the applicant is that the PCR protocol disclosed herein is effective in amplifying target sequences obtained from slide-mounted FFPE tissue samples prepared using the methods and compositions disclosed herein. As will be discussed in more detail in the following sections, the amplified sequences obtained from the aforementioned PCR protocol are uniform and high in quantity.

FIG. 3A is a black-and-white image of an example of a FFPE tissue sample 300 mounted or fixed on a solid substrate 302. The solid substrate 302 can be a support or backing made in part of an inert material. As previously discussed, the solid substrate 302 can be a slide such as a microscope slide. In some embodiments, the solid substrate 302 can be a glass microscope slide, an inert polymeric or plastic microscope slide, or a combination thereof. More specifically, the solid substrate 302 can be a fused silica microscope slide, a polystyrene microscope slide, or an acrylic microscope slide.

The position of the FFPE tissue sample 300 on the solid substrate 302 is shown by the dotted circle. The FFPE tissue sample 300 can appear as a white or gray layer or film covering part of the solid substrate 302. The underlying tissue sample can be obscured by the white or cloudy paraffin wax used to fix the tissue sample to the solid substrate 302. The FFPE tissue sample 300 can have a thickness of between about 4 µm and 10 µm as measured from the surface of the solid substrate 302.

In certain embodiments, the solid substrate 302 can have a length dimension of about 75.0 mm and a width dimension of about 25.0 mm for a total surface area of about 1,875 mm$^2$. In some embodiments, the FFPE tissue sample 300 can take up between approximately 100 mm$^2$ to approximately 200 mm$^2$ of this total surface area.

The FFPE tissue sample 300 on the solid substrate 302 can be stored in a cold storage receptacle such as a refrigerator, a refrigerated storage, a cooler or cooling container, or a combination thereof prior to being used in the methods disclosed herein. Alternatively, the FFPE tissue sample 300 on the solid substrate 302 can be stored at room temperature (or between about 20° C. and about 25° C.) prior to being used.

The methods (e.g., method 200) and compositions disclosed herein can be successfully applied to a variety of FFPE tissue samples 300. For example, the methods and compositions disclosed herein can be used to prepare DNA libraries from FFPE bladder tissue samples, FFPE breast tissue samples, FFPE cervical tissue samples, FFPE colorectal tissue samples, FFPE esophageal tissues samples, FFPE gastric tissue samples, FFPE renal tissue samples, FFPE hepatic tissue samples, FFPE lung squamous tissue samples, FFPE lymphoid tissue samples, FFPE skin tissue sample (e.g., FFPE malignant melanoma tissue sample), FFPE nasopharyngeal tissue samples, FFPE ovarian tissue samples, FFPE prostate tissue samples, and FFPE thyroid tissue samples.

Figure 3B:
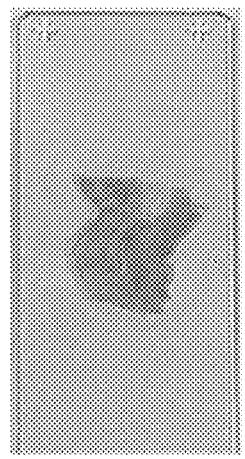
FIG. 3B is a black-and-white image of a deparaffinized slide-mounted FFPE tissue sample.

FIG. 3B is a black-and-white image of a deparaffinized slide-mounted FFPE tissue sample offered for comparison. For example, the slide-mounted FFPE tissue sample shown in FIG. 3B can be deparaffinized by submerging the entire slide comprising the FFPE tissue sample in xylene. The slide comprising the FFPE tissue sample can then be washed with ethanol. At this point, the deparaffinized tissue sample can then be scraped off with a scalpel or razor blade for further processing with additional reagents.

FIG. 4A illustrates a pipette 400 aspirating a reagent mixture 402 into a pipette tip 404 coupled to the pipette 400. In some embodiments, the pipette 400 can be a fixed-volume micropipette or an adjustable-volume micropipette. For example, the pipette 400 can be a Rainin Pipet-Lite® manual single-channel pipette distributed by Mettler-Toledo Rainin, LLC. Other micropipettes such as those distributed by Thermo Fisher Scientific Inc. and Sigma-Aldrich, Inc. can also be used. In some embodiments, the pipette tip 404 can be a wide orifice pipette tip 900 (see FIG. 9). The wide orifice pipette tip 900 will be discussed in more detail in the following sections.

FIG. 4A also illustrates that the reagent mixture 402 can comprise a reagent solution 406, a primer pool solution 408, and deionized water 410. In one embodiment, the reagent mixture 402 can comprise a 50% (v/v) 2× reagent solution 406, a 20% (v/v) 5× primer pool solution 408, and 30% deionized water 410. For example, a 20 µL, volume of the reagent mixture 402 can be made by pipetting 10 µL, of the 2× reagent solution 406, 4 µL of the 5× primer pool solution 408, and 6 µL of deionized water 410 into a standalone or single reaction tube or test tube. The reagent mixture 402 can then be thoroughly mixed and/or centrifuged and the entire 20 µL volume of the reagent mixture 402 can be aspirated into the pipette tip 404 for delivery onto a slide-mounted FFPE tissue sample 300.

FIG. 4B illustrates the pipette 400 applying a droplet 412 of the reagent mixture 402 onto a FFPE tissue sample 300 mounted or fixed on a solid substrate 302. As previously discussed, the solid substrate 302 can be a glass slide (e.g., a glass microscope slide), an inert polymeric slide, or a combination thereof.

The pipette 400 can apply the droplet 412 of the reagent mixture 402 onto the FFPE tissue sample 300 by dispensing the droplet 412 from the pipette tip 404 directly onto a surface of the FFPE tissue sample 300. In some embodiments, the pipette tip 404 can be a wide orifice pipette tip 900.

The droplet 412 can be applied to the middle or a center portion of the FFPE tissue sample 300. In certain embodiments, the droplet 412 can have a droplet volume of between 10 µL and 30 µL. For example, the droplet 412 can have a droplet volume of about 20 µL.

The droplet 412 of the reagent mixture 402 can be applied on to the slide-mounted FFPE tissue sample 300 after the FFPE tissue sample 300 is retrieved from a cold storage receptacle such as a refrigerator, a refrigerated storage, a cooler or cooling container, or a combination thereof. In these embodiments, the FFPE tissue sample 300 can be at a temperature of between about 0° C. and about 20° C. Alternatively, the FFPE tissue sample 300 can be allowed to thaw or come to room temperature after being retrieved from the cold storage receptacle. In this case, the droplet 412 of the reagent mixture 402 can be applied on to the slide-mounted FFPE tissue sample 300 when the FFPE tissue sample 300 is at room temperature (or between about 20° C. and about 25° C.).

Figure 5:
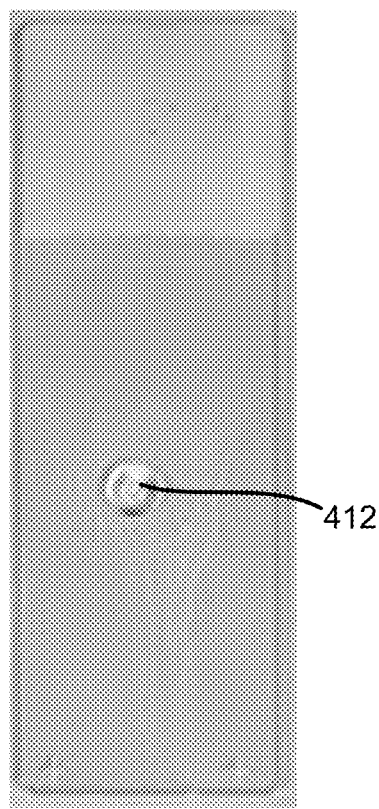
FIG. 5 is a black-and-white image of a droplet of the reagent mixture on a microscope slide.

FIG. 5 is a black-and-white image of a droplet 412 of the reagent mixture 402 on a glass microscope slide serving as the solid substrate 302. As can be seen in FIG. 5, the droplet 412 of the reagent mixture 402 can initially form a bead when applied onto the surface of a glass microscope slide. In some embodiments, the droplet 412 can initially only take up between about 4.0 mm$^2$ to about 5.0 mm$^2$ of space on the surface of the glass microscope slide when first applied to the glass microscope slide.

Figure 6A:
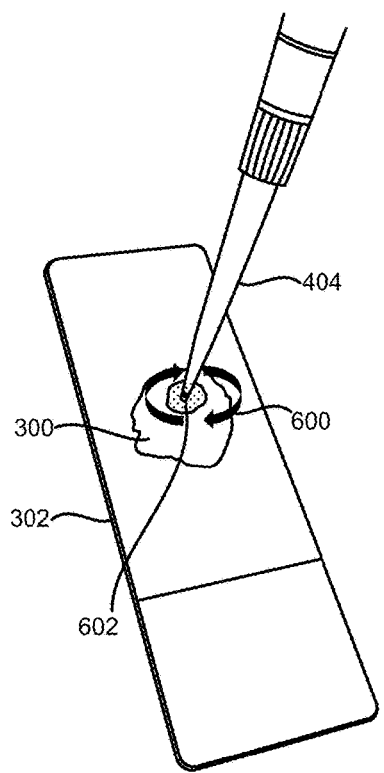
FIG. 6A illustrates a pipette tip used to stir the droplet of the reagent mixture on the slide while scraping the FFPE tissue sample mounted on the slide.

FIG. 6A illustrates a pipette tip 404 used to stir the droplet 412 of the reagent mixture 402 on the solid substrate 302 while scraping the FFPE tissue sample 300 mounted on the solid substrate 302. As shown in FIG. 6A, the solid substrate 302 can be a slide such as a glass microscope slide. In some embodiments, the pipette tip 404 can be a wide orifice pipette tip 900.

Scraping the FFPE tissue sample 300 mounted or fixed on the solid substrate 302 can be done simultaneously with stirring the droplet 412 of the reagent mixture 402 on the solid substrate 302. The FFPE tissue sample 300 can be scraped or broken up with a distal end of the pipette tip 404. More specifically, the FFPE tissue sample 300 can be scraped or broken up with an edge of the distal end of the pipette tip 404. In some embodiments, the FFPE tissue sample 300 can be scraped with a distal end of a wide orifice pipette tip 900. The FFPE tissue sample 300 can be scraped or broken up with the edge of the distal end of the pipette tip 404 while a segment of the pipette tip 404 proximal to the distal end is used to stir the droplet 412.

The same pipette tip 404 (see FIG. 4B) used to apply the droplet 412 can be used to stir the droplet 412 on the solid substrate 302 while simultaneously scraping portions of the slide-mounted FFPE tissue sample 300. For example, the same wide orifice pipette tip 900 used to apply the droplet 412 can also be used to stir the droplet 412 of the reagent mixture 402 on the solid substrate 302 while simultaneously scraping portions of the slide-mounted FFPE tissue sample 300 into the stirred droplet 412.

In some embodiments, the droplet 412 of the reagent mixture 402 can be stirred on the solid substrate 302 in a circular motion 600. More specifically, the droplet 412 of the reagent mixture 402 can be stirred on the solid substrate 302 in a clockwise circulation motion, a counterclockwise circular motion, or a combination thereof.

When the droplet 412 is stirred in a substantially circular motion 600 using the pipette tip 404, the stirring area or stirring region on the solid substrate 302 can be a substantially circular area or region. For example, in one embodiment, the droplet 412 can be stirred in a substantially circular area of between about 12.0 mm$^2$ and about 20.0 mm$^2$ (i.e., the stirring is confined to a substantially circular region of the solid substrate 302 having an area of between about 12.0 mm$^2$ and about 20.0 mm$^2$). In other embodiments, the droplet 412 can be stirred in a substantially circular area of between about 20.0 mm$^2$ and about 40.0 mm$^2$.

In other embodiments, the droplet 412 can also be stirred in a rectangular motion, an elliptic motion, a zig-zig motion, a spiraling motion, a figure-eight motion, or a combination thereof. The objective of the stirring and scraping is to create a reaction mixture 602 comprising the reagent mixture 402 and small pieces of the FFPE tissue sample 300. The reaction mixture 602 can be in the form of a slurry or viscous solution.

The droplet 412 can be stirred and the FFPE tissue sample 300 can be scraped for between about 1 minute and about 5 minutes in order to form the reaction mixture 602. More specifically, the droplet 412 can be stirred and the FFPE tissue sample 300 can be scraped for between about 2 minutes and about 3 minutes in order to form the reaction mixture 602. The reaction mixture 602 can be formed by incorporating broken up pieces of the FFPE tissue sample 300 into the reagent mixture 402 such that a slurry or viscous solution is formed comprising both the reagent mixture 402 and pieces of the FFPE tissue sample 300. The reaction mixture 602 can be formed on the solid substrate 302 before aspirating the reaction mixture 602 into the pipette tip 404.

Another unexpected discovery made by the applicant is that multiple DNA libraries can be generated from one slide-mounted FFPE tissue sample 300 using the methods and compositions disclosed herein. Since the method does not require deparaffinization, multiple wash steps, or scraping the sample off the slide into a reaction tube, a clinician or laboratory technician can apply one droplet 412 of the reagent mixture 402 on one part of the FFPE tissue sample 300 and localize the stirring and scraping to that part of the FFPE tissue sample 300. Once that reaction mixture 602 is aspirated into the pipette tip 404, another droplet 412 of the reagent mixture 402 can be applied to an unperturbed part of the FFPE tissue sample 300 to form another reaction mixture 602. This is especially beneficial when biopsied FFPE tissue samples are rare or difficult to obtain.

Figure 6B:
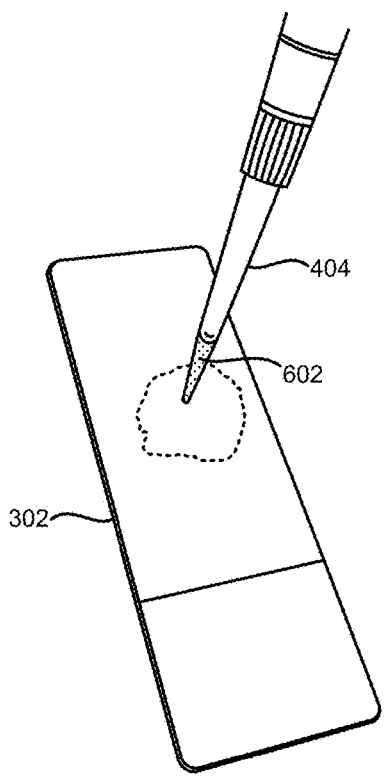
FIG. 6B illustrates the pipette tip aspirating a reaction mixture comprising the reagent mixture and a portion of the FFPE tissue sample into the pipette tip.

FIG. 6B illustrates a pipette tip 404 aspirating a reaction mixture 602 comprising the reagent mixture 402 and portions of the scraped FFPE tissue sample 300 from the solid substrate 302 directly into the pipette tip 404. As previously discussed, the pipette tip 404 can be a wide orifice pipette tip 900. In some embodiments, the pipette tip 404 used to aspirate the reaction mixture 602 can be the same pipette tip 404 used to stir the droplet 412 and scrape the FFPE tissue sample 300 mounted or fixed on the solid substrate 302.

The reaction mixture 602 can be aspirated by drawing the pipette tip 404 over the stirred area in a substantially circular motion while slowly releasing a depressed plunger of the pipette 400. In other embodiments, the reaction mixture 602 can also be aspirated by drawing the pipette tip 404 over the stirred area in a substantially rectangular motion, an elliptic motion, a zig-zag motion, a spiraling motion, a figure-eight motion, or a combination thereof while slowly releasing a depressed plunger of the pipette 400.

In some embodiments, the reaction mixture 602 aspirated or drawn by the pipette tip 404 can be about 20 µL. In other embodiments, the reaction mixture 602 aspirated or drawn by the pipette tip 404 can be between about 15 µL and about 25 µL. The volume of the reaction mixture 602 aspirated can depend on the volume of the droplet 412 of the reagent mixture 402 initially applied to the FFPE tissue sample 300.

Figure 7:
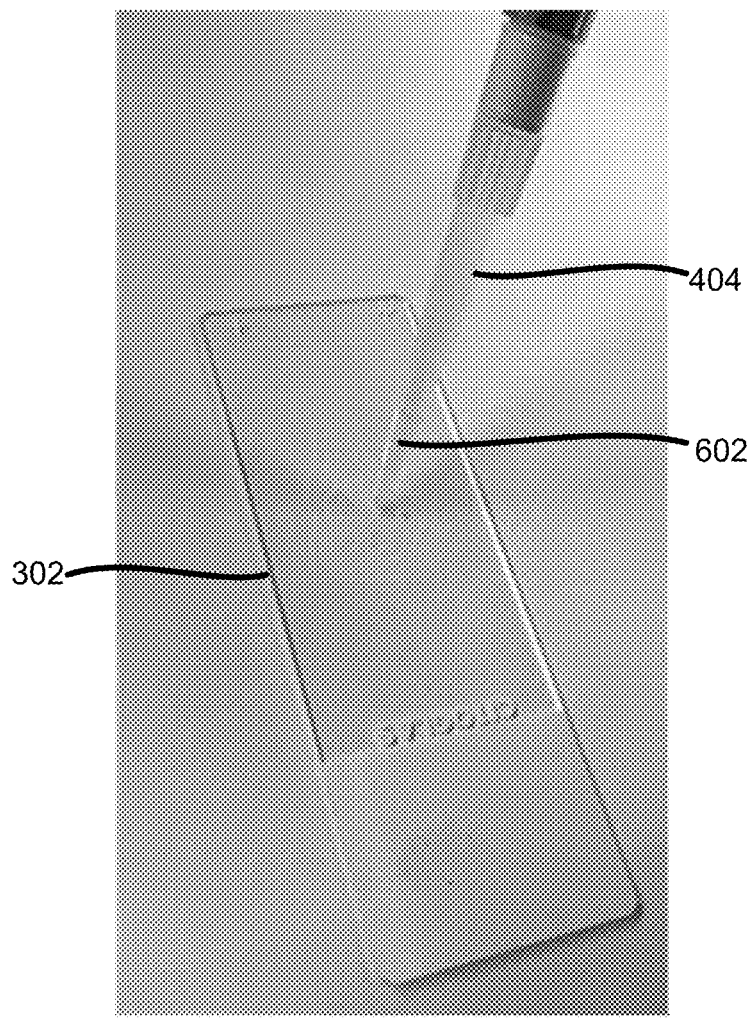
FIG. 7 is a black-and-white image of a pipette tip having aspirated the reaction mixture from a slide.

FIG. 7 is a black-and-white image of a pipette tip 404 having aspirated the reaction mixture 602 directly from a glass microscope slide into the pipette tip 404. In some embodiments, some portions of the FFPE tissue sample 300 can still remain on the solid substrate 302 (e.g., the glass slide) even after the reaction mixture 602 (or a portion thereof) has been aspirated from the solid substrate 302.

Figure 8A:
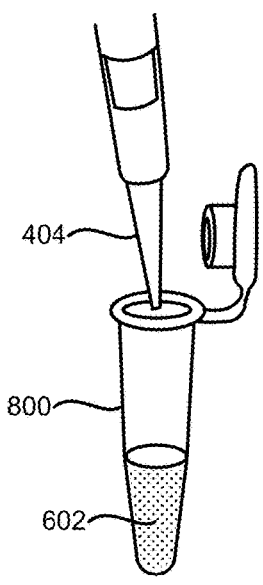
FIG. 8A illustrates a pipette tip dispensing the reaction mixture into a standalone reaction vessel.
Figure 8B:
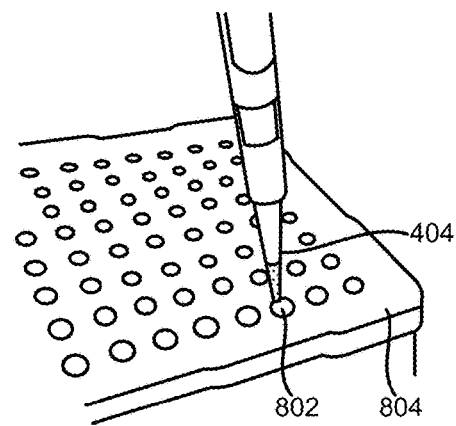
FIG. 8B illustrates a pipette tip dispensing the reaction mixture into a reaction well of a multi-well plate.

FIGS. 8A and 8B each illustrate a pipette tip 404 dispensing the reaction mixture 602 into a reaction vessel. The reaction vessel can refer to a standalone reaction vessel 800 or a reaction well 802 of a multi-well plate 804. For example, as depicted in FIG. 8A, the standalone reaction vessel 800 or can be a singular PCR reaction tube or vessel. Moreover, as depicted in FIG. 8B, the reaction well 802 can be one well of a multi-well PCR plate. For example, the multi-well plate 804 can be 96-well plate or a 384-well plate. Once the reaction mixture 602 is within the standalone reaction vessel 800 or the reaction well 802, the reaction mixture 602 can be considered a PCR mixture or a PCR-ready mixture. The reaction mixture 602 in the reaction vessel can then be subjected to a PCR protocol such as the hot start PCR protocol described herein.

Figure 9:
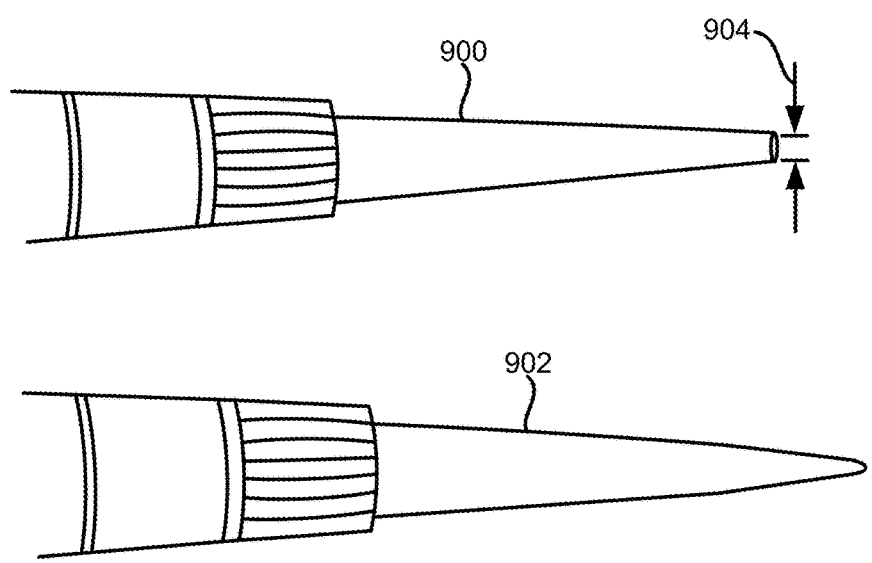
FIG. 9 illustrates an embodiment of a wide orifice pipette tip compared to a conventional pipette tip.

FIG. 9 illustrates an embodiment of a wide orifice pipette tip 900 compared to a conventional pipette tip 902. As previously discussed, the wide orifice pipette tip 900 can be used to apply the droplet 412 of the reagent mixture 402 to the FFPE tissue sample 300, stir the droplet 412, scrape the FFPE tissue sample 300, and aspirate the reaction mixture 602 directly from the solid substrate 302 into the wide orifice pipette tip 900.

In some embodiments, the wide orifice pipette tip 900 can be a disposable pipette tip. The wide orifice pipette tip 900 can have an orifice diameter wider than a conventional pipette tip 902.

As shown in FIG. 9, the wide orifice pipette tip 900 can have an orifice inner diameter 904. In some embodiments, the wide orifice pipette tip 900 can have an orifice inner diameter 904 of between about 1.00 mm and 1.25 mm. More specifically, the wide orifice pipette tip 900 can have an orifice inner diameter 904 of between 1.10 mm and 1.20 mm.

One unexpected discovery made by the applicant is that wide orifice pipette tips 900 are ideal for applying the droplet 412 of the reagent mixture 402, stirring the droplet 412 on the solid substrate 302 (e.g., glass microscope slide), and aspirating the reaction mixture 602 or slurry formed from the reagent mixture 402 and the pieces of FFPE tissue sample 300 back into the wide orifice pipette tip 900. For example, both the reagent mixture 402 and the reaction mixture 602 are somewhat viscous solutions that are not easily aspirated or dispensed by conventional pipette tips 902. Moreover, the greater circumference of the wide orifice pipette tip 900 gives the pipette tip more edge surface to scrape the FFPE tissue sample 300.

Figure 10:
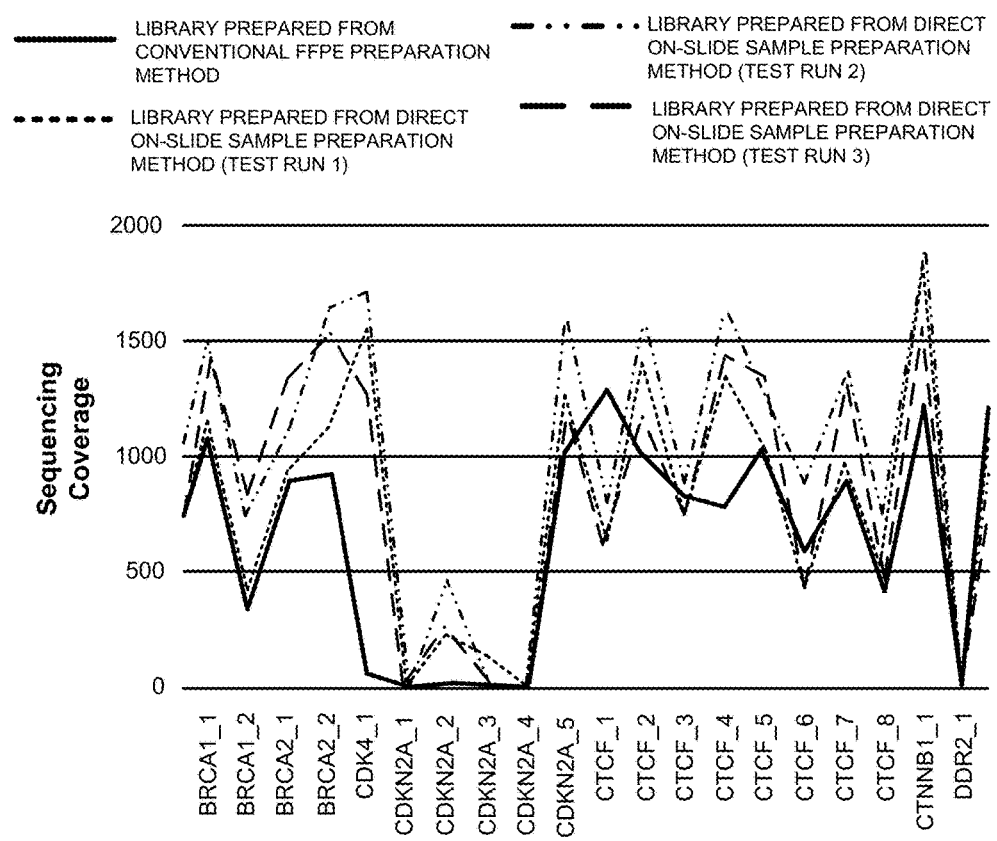
FIG. 10 is a graph illustrating sequence coverage profiles of a DNA library prepared from a conventional FFPE preparation method and DNA libraries prepared using the methods and compositions disclosed herein.

FIG. 10 is a graph illustrating sequence coverage profiles of a DNA library prepared using a conventional FFPE preparation kit and DNA libraries prepared using the methods and compositions disclosed herein. All sequencing coverage data shown in FIG. 10 were obtained using an Ion Personal Genome Machine® (PGM) system distributed by Thermo Fisher Scientific Inc.

The solid line shown in FIG. 10 represents a sequence coverage profile of a DNA library prepared using a popular conventional FFPE preparation kit (e.g., the Ion AmpliSeq® Direct FFPE DNA Kit) while the remaining three broken lines represent sequence coverage profiles of DNA libraries prepared using the methods and compositions disclosed herein. All such DNA libraries were prepared using slide-mounted FFPE tissue samples obtained from the same source tissue. As depicted in FIG. 10, the sequence coverage profiles of DNA libraries prepared using the methods and compositions disclosed herein generally matched the sequence coverage profile of the DNA library prepared using the popular conventional FFPE preparation kit. In addition, the sequence coverage profiles of DNA libraries prepared using the methods and compositions disclosed herein also maintained a high-level of precision with one another.

Also important to note here is that the DNA libraries prepared using the methods and compositions disclosed herein were each prepared in a shorter period of time and without cumbersome multi-step DNA extraction or purification steps. In addition, the DNA libraries prepared using the methods and compositions disclosed herein also required much less FFPE tissue starting material.

Figure 11:
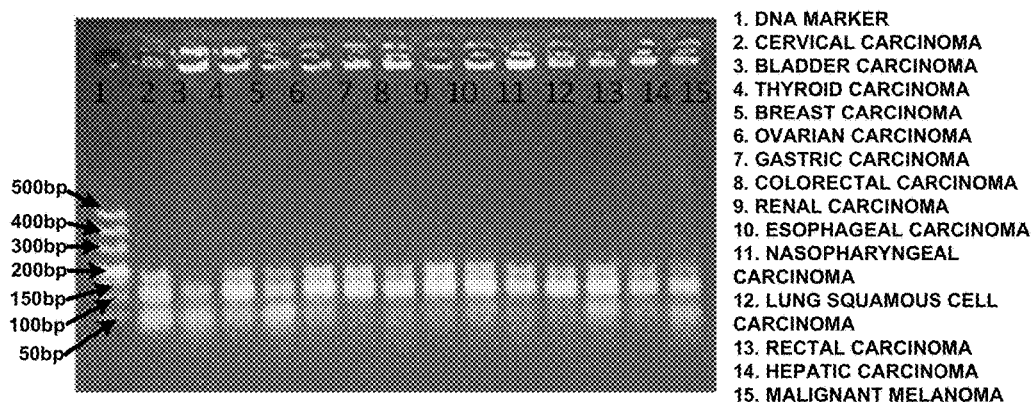
FIG. 11 is an annotated black-and-white image of a gel electrophoresis showing base pair lengths of target sequences in DNA libraries prepared from various FFPE tissue samples using the methods and compositions disclosed herein.

FIG. 11 is an annotated black-and-white image of a gel electrophoresis showing base pair lengths of amplicons in DNA libraries prepared from various FFPE tissue samples using the methods and compositions disclosed herein. As indicated in FIG. 11, the DNA libraries were prepared from various types of tissue samples showing signs of cancerous growth. For example, as indicated in FIG. 11, DNA libraries were prepared from FFPE cervical tissue, bladder tissue, thyroid tissue, breast tissue, ovarian tissue, gastric tissue, colorectal tissue, renal tissue, esophageal tissue, nasopharyngeal tissue, lung tissue, rectal tissue, hepatic tissue, and skin tissue.

All such DNA libraries were prepared using the same primer pool comprising about 200 pairs of forward and reverse primers. All such primers were designed to result in amplicons of approximately 100 to 200 base pairs (bp). The gel electrophoresis shows that DNA libraries prepared from the 14 tissue samples indicated contained primarily of amplicons of approximately 100 to 200 bp. FIG. 11 provides further evidence that the library preparation methods and compositions disclosed herein works equally well on different types of FFPE tissue samples.

Figure 12:
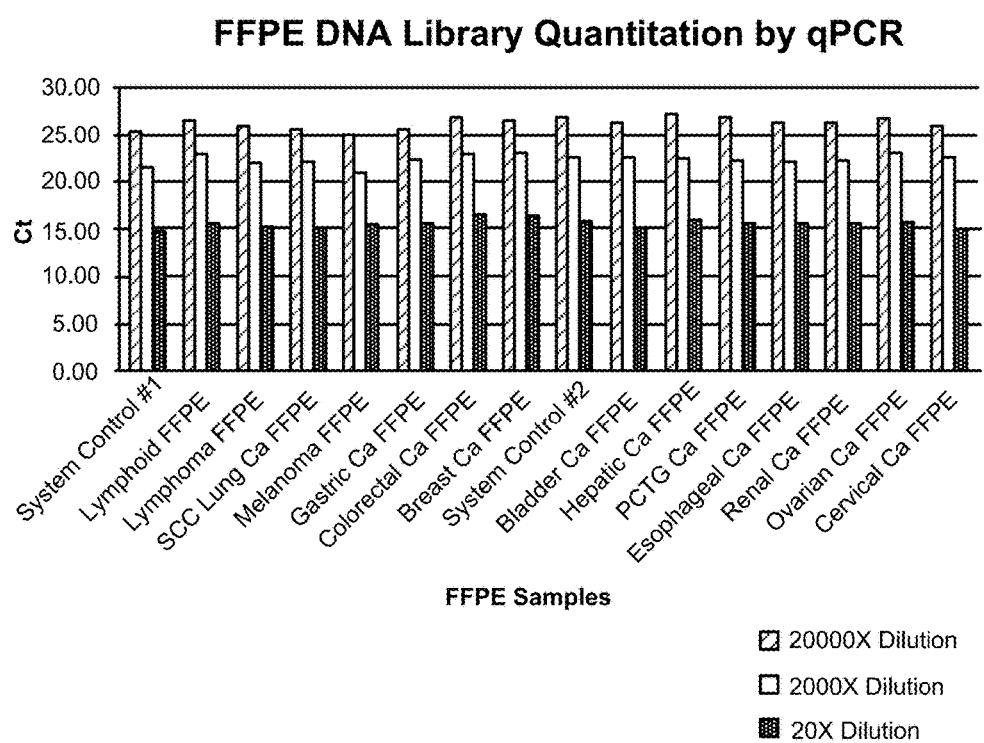
FIG. 12 is a graph illustrating the results of quantitation assays done by qPCR of DNA libraries prepared using the methods and compositions disclosed herein.

FIG. 12 is a graph illustrating the results of quantitation assays done by quantitative real-time PCR (qPCR) of multiple DNA libraries prepared from a wide range of FFPE tissue samples. All such DNA libraries (other than the system controls) were prepared using the methods and compositions disclosed herein. Such quantitation assays were done using the Ion Library TaqMan® Quantitation Kit distributed by Thermo Fisher Scientific Inc. As depicted in FIG. 12, DNA libraries were quantitated and compared against system controls (e.g., an *E. coli* DH10B control library) provided by the quantitation kit. All DNA libraries (including system controls) were diluted by dilution amounts of 1:20, 1:2000, and 1:20000 and the same primer pools were used to prepare such libraries. Also, since cycle threshold (or Ct) values are inverse to the amount of target sequences in a sample, the greater the dilution amount, the higher the Ct value should be for such a sample.

The results of such quantitation assays show that target sequence amounts were consistent across all libraries. Moreover, as seen in FIG. 12, all Ct values of such libraries closely aligned with system controls and any differences were within expected error ranges.

Each of the individual variations or embodiments described and illustrated herein has discrete components and features which may be readily separated from or combined with the features of any of the other variations or embodiments. Modifications may be made to adapt a particular situation, material, composition of matter, process, process act(s) or step(s) to the objective(s), spirit or scope of the present invention.

Methods recited herein may be carried out in any order of the recited events that is logically possible, as well as the recited order of events. Moreover, additional steps or operations may be provided or steps or operations may be eliminated to achieve the desired result.

Furthermore, where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

This disclosure is not intended to be limited to the scope of the particular forms set forth, but is intended to cover alternatives, modifications, and equivalents of the variations or embodiments described herein. Further, the scope of the disclosure fully encompasses other variations or embodiments that may become obvious to those skilled in the art in view of this disclosure.

What is claimed is:

1. A method of preparing a deoxyribonucleic acid (DNA) library for downstream next-generation sequencing, comprising:
    applying a droplet of a reagent mixture onto a formalin-fixed paraffin-embedded (FFPE) tissue sample, wherein the FFPE tissue sample is mounted on a slide, wherein the reagent mixture comprises:
        a reagent solution comprising:
            one or more buffer solutions,
            a cofactor,
            a nonionic surfactant,
            a glycerol solution,
            a gelatin solution,
            dNTPs, and
            a DNA polymerase; and
        a primer pool comprising a plurality of forward primers and reverse primers;
    stirring the droplet of the reagent mixture in a circular motion on the slide while scraping portions of the FFPE tissue sample mounted on the slide to yield a reaction mixture comprising the reagent mixture and portions of the FFPE tissue sample;
    aspirating the reaction mixture from the slide directly into a pipette tip and dispensing the reaction mixture into a reaction vessel;
    subjecting the reaction mixture in the reaction vessel to a polymerase chain reaction (PCR) protocol, wherein the PCR protocol comprises the steps of:
        (i) heating the reaction mixture at a first temperature to activate the DNA polymerase in an activation step;
        (ii) further heating the reaction mixture at a second temperature to denature nucleic acids within the reaction mixture in a denaturation step;
        (iii) lowering the temperature to a third temperature to allow for annealing and extension; and
        (iv) repeating steps (ii) and (iii) for at least 24 cycles.

2. The method of claim 1, further comprising:
    applying the droplet of the reagent mixture onto the FFPE tissue sample using a wide orifice pipette tip coupled to a pipette;
    using the same wide orifice pipette tip to stir the droplet of the reagent mixture on the slide while scraping the portion of the FFPE tissue sample mounted on the slide; and
    aspirating the reaction mixture into the wide orifice pipette tip, wherein the wide orifice pipette tip has an orifice inner diameter of between about 1.00 mm to about 1.25 mm.

3. The method of claim 1, further comprising stirring the droplet of the reagent mixture on the slide in a clockwise circular motion, a counterclockwise circular motion, or a combination thereof.

4. The method of claim 1, wherein the droplet of the reagent mixture applied onto the FFPE tissue sample is about 20 microliters (μL) in volume.

5. The method of claim 1, wherein the droplet of the reagent mixture is applied on to the FFPE tissue sample when the FFPE tissue sample is at a temperature of between about 0° C. and about 23° C.

6. The method of claim 1, stirring the droplet of the reagent mixture on the slide while scraping the portion of the FFPE tissue sample mounted on the slide for between about 1 minute to about 5 minutes prior to aspirating the reaction mixture.

7. The method of claim 1, wherein the PCR protocol is a hot start PCR protocol and wherein the first temperature of the hot start PCR protocol is about 95° C., the second temperature of the PCR protocol is about 99° C., and the third temperature of the hot start PCR protocol is about 60° C.

8. A method of preparing a polymerase chain reaction (PCR) mixture comprising a formalin-fixed paraffin-embedded (FFPE) tissue sample, the method comprising:
    applying a droplet of a reagent mixture to a formalin-fixed paraffin-embedded (FFPE) tissue sample, wherein the FFPE tissue sample is mounted on a slide, wherein the reagent mixture comprises:
        a reagent solution comprising:
            a tris(hydroxymethyl)aminomethane (Tris)-hydrochloric acid (HCl) buffer solution,
            a potassium chloride (KCl) buffer solution,
            a magnesium chloride ($MgCl_2$) solution,
            a non-ionic surfactant solution,
            a glycerol solution,
            a gelatin solution,
            dNTPs, and
            a Taq DNA polymerase; and
        a primer pool comprising a plurality of forward primers and reverse primers;
    stirring the droplet of the reagent mixture in a circular motion on the slide while scraping portions of the FFPE tissue sample mounted on the slide to yield a PCR mixture comprising the reagent mixture and portions of the FFPE tissue sample; and aspirating the PCR mixture from the slide directly into a pipette tip and dispensing the PCR mixture into a reaction vessel.

9. The method of claim 8, further comprising:
applying the droplet of the reagent mixture onto the FFPE tissue sample using a wide orifice pipette tip coupled to a pipette;
using the same wide orifice pipette tip to stir the droplet of the reagent mixture on the slide while scraping the portion of the FFPE tissue sample mounted on the slide; and
aspirating the PCR mixture into the wide orifice pipette tip,
wherein the wide orifice pipette tip has an orifice inner diameter of between about 1.00 mm to about 1.25 mm.

10. The method of claim 8, further comprising stirring the droplet of the reagent mixture on the slide in a clockwise circular motion, a counterclockwise circular motion, or a combination thereof.

11. The method of claim 8, wherein the droplet of the reagent mixture applied onto the FFPE tissue sample is about 20 microliters (µL) in volume.

12. The method of claim 8, wherein the droplet of the reagent mixture is applied on to the FFPE tissue sample when the FFPE tissue sample is at a temperature of between about 0° C. and about 23° C.

13. The method of claim 8, stirring the droplet of the reagent mixture on the slide while scraping the portion of the FFPE tissue sample mounted on the slide for between about 1 minute to about 5 minutes prior to aspirating the PCR mixture.

14. The method of claim 8, wherein the FFPE tissue sample is at least one of a FFPE bladder tissue sample, a FFPE breast tissue sample, a FFPE cervical tissue sample, a FFPE colorectal tissue sample, a FFPE esophageal tissues sample, a FFPE gastric tissue sample, a FFPE renal tissue sample, a FFPE hepatic tissue sample, a FFPE lung squamous tissue sample, a FFPE lymphoid tissue sample, a FFPE skin tissue sample, a FFPE nasopharyngeal tissue sample, a FFPE ovarian tissue sample, a FFPE prostate tissue sample, and a FFPE thyroid tissue sample.

* * * * *